US 9,295,280 B2
Mar. 29, 2016

(12) United States Patent
Jacofsky et al.

(10) Patent No.: US 9,295,280 B2
(45) Date of Patent: Mar. 29, 2016

(54) METHOD AND APPARATUS FOR COLD PLASMA FOOD CONTACT SURFACE SANITATION

(71) Applicant: Cold Plasma Medical Technologies, Inc., Scottsdale, AZ (US)

(72) Inventors: Marc C. Jacofsky, Phoenix, AZ (US); Gregory A. Watson, Sanford, FL (US)

(73) Assignee: Plasmology4, Inc., Scottsdale, AZ (US)

( * ) Notice: Subject to any disclaimer, the term of this patent is extended or adjusted under 35 U.S.C. 154(b) by 68 days.

(21) Appl. No.: 14/103,540

(22) Filed: Dec. 11, 2013

(65) Prior Publication Data
US 2014/0161947 A1 Jun. 12, 2014

Related U.S. Application Data

(60) Provisional application No. 61/735,804, filed on Dec. 11, 2012.

(51) Int. Cl.
*A61L 2/14* (2006.01)
*A23L 3/26* (2006.01)
*A23B 4/015* (2006.01)
*A23B 9/06* (2006.01)
*A23B 7/015* (2006.01)
*A61L 2/00* (2006.01)
(Continued)

(52) U.S. Cl.
CPC . *A23L 3/26* (2013.01); *A23B 4/015* (2013.01); *A23B 7/015* (2013.01); *A23B 9/06* (2013.01); *A23L 3/32* (2013.01); *A61L 2/00* (2013.01); *A61L 2/14* (2013.01); *A61L 9/00* (2013.01)

(58) Field of Classification Search
CPC ........ A23B 4/015; A23B 5/015; A23B 7/015; A23B 9/06; A23L 3/32; A23L 3/325; A61L 2/03–2/035; A61L 2202/11; A61L 2202/20; A61L 9/22; A61L 2/14; A61L 3/26; A61L 9/00; A61L 2/00
USPC ........................ 426/244–247; 99/451; 422/22
See application file for complete search history.

(56) References Cited

U.S. PATENT DOCUMENTS 2,927,322 A 3/1960 Simon et al.
3,432,722 A 3/1969 Naydan et al.
(Continued)

FOREIGN PATENT DOCUMENTS

WO WO 2005/084569 A1 9/2005
WO WO 2006/116252 11/2006
(Continued)

OTHER PUBLICATIONS

International Search Report issued Apr. 14, 2014 for Appl. No. PCT/US2013/074437, 3 pages.
(Continued)

*Primary Examiner* — Drew Becker
(74) *Attorney, Agent, or Firm* — Sterne, Kessler, Goldstein & Fox P.L.L.C.

(57) ABSTRACT

A cold plasma device for killing or reducing a microbiological pathogen, or denaturing a protein in food, in a food processing system using a cold plasma device. The cold plasma device directs a cold plasma at food or a food surface over an effective area for an effective amount of time. The cold plasma device can be a DBD electrode device, or an army of DBD electrode devices. A grounding rod assembly is also described.

24 Claims, 10 Drawing Sheets

(51) Int. Cl.
*A61L 9/00* (2006.01)
*A23L 3/32* (2006.01)

(56) References Cited

U.S. PATENT DOCUMENTS

| | | | |
|---|---|---|---|
| 3,487,414 A | 12/1969 | Booker | |
| 3,735,591 A | 5/1973 | Burkhart | |
| 4,088,926 A | 5/1978 | Fletcher et al. | |
| 4,365,622 A | 12/1982 | Harrison | |
| 4,380,320 A | 4/1983 | Hollstein et al. | |
| 4,422,013 A | 12/1983 | Turchi et al. | |
| 5,079,482 A | 1/1992 | Villecco et al. | |
| 5,216,330 A | 6/1993 | Ahonen | |
| 5,225,740 A | 7/1993 | Ohkawa | |
| 5,304,888 A | 4/1994 | Gesley et al. | |
| 5,698,164 A | 12/1997 | Kishioka et al. | |
| 5,876,663 A | 3/1999 | Laroussi | |
| 5,883,470 A | 3/1999 | Hatakeyama et al. | |
| 5,909,086 A | 6/1999 | Kim et al. | |
| 5,961,772 A * | 10/1999 | Selwyn | 156/345.39 |
| 5,977,715 A | 11/1999 | Li et al. | |
| 6,096,564 A | 8/2000 | Denes et al. | |
| 6,099,523 A | 8/2000 | Kim et al. | |
| 6,113,851 A | 9/2000 | Soloshenko et al. | |
| 6,204,605 B1 | 3/2001 | Laroussi et al. | |
| 6,225,593 B1 | 5/2001 | Howieson et al. | |
| 6,228,330 B1 * | 5/2001 | Herrmann et al. | 422/186.05 |
| 6,262,523 B1 | 7/2001 | Selwyn et al. | |
| 6,441,554 B1 | 8/2002 | Nam et al. | |
| 6,455,014 B1 | 9/2002 | Hammerstrom et al. | |
| 6,611,106 B2 | 8/2003 | Monkhorst et al. | |
| 6,667,007 B1 | 12/2003 | Schmidt | |
| 6,956,329 B2 | 10/2005 | Brooks et al. | |
| 6,958,063 B1 | 10/2005 | Soll et al. | |
| 7,006,874 B2 | 2/2006 | Knowlton et al. | |
| 7,011,790 B2 | 3/2006 | Ruan et al. | |
| 7,037,468 B2 | 5/2006 | Hammerstrom et al. | |
| 7,081,711 B2 | 7/2006 | Glidden et al. | |
| 7,094,314 B2 | 8/2006 | Kurunczi | |
| 7,192,553 B2 | 3/2007 | Crowe et al. | |
| 7,215,697 B2 | 5/2007 | Hill | |
| 7,271,363 B2 | 9/2007 | Lee et al. | |
| 7,300,436 B2 | 11/2007 | Penny et al. | |
| 7,608,839 B2 | 10/2009 | Coulombe et al. | |
| 7,633,231 B2 * | 12/2009 | Watson | H05H 1/46 219/121.36 |
| 7,683,342 B2 | 3/2010 | Morfill et al. | |
| 7,691,101 B2 | 4/2010 | Davison et al. | |
| 7,719,200 B2 | 5/2010 | Laroussi | |
| 7,777,151 B2 | 8/2010 | Kuo | |
| 7,785,322 B2 | 8/2010 | Penny et al. | |
| 7,799,290 B2 | 9/2010 | Hammerstrom et al. | |
| 8,267,884 B1 | 9/2012 | Hicks | |
| 8,294,369 B1 | 10/2012 | Laroussi | |
| 8,460,283 B1 | 6/2013 | Laroussi et al. | |
| 2002/0129902 A1 | 9/2002 | Babayan et al. | |
| 2003/0129107 A1 * | 7/2003 | Denes et al. | 422/186.21 |
| 2003/0222586 A1 | 12/2003 | Brooks et al. | |
| 2005/0031485 A1 * | 2/2005 | Wen | 422/28 |
| 2005/0056596 A1 * | 3/2005 | Paskalov et al. | 210/748 |
| 2005/0088101 A1 | 4/2005 | Glidden et al. | |
| 2005/0179395 A1 | 8/2005 | Pai | |
| 2006/0156983 A1 * | 7/2006 | Penelon et al. | 118/723 E |
| 2006/0189976 A1 | 8/2006 | Karni et al. | |
| 2007/0261570 A1 * | 11/2007 | Mole | 99/467 |
| 2008/0159925 A1 | 7/2008 | Shimizu et al. | |
| 2009/0188626 A1 | 7/2009 | Lu et al. | |
| 2010/0133979 A1 | 6/2010 | Lu | |
| 2010/0243410 A1 | 9/2010 | Hall et al. | |
| 2010/0284867 A1 * | 11/2010 | Konesky | 422/186.06 |
| 2011/0014330 A1 * | 1/2011 | Meyers et al. | 426/236 |
| 2011/0022043 A1 | 1/2011 | Wandke et al. | |
| 2011/0048251 A1 | 3/2011 | Bardenshtein et al. | |
| 2012/0100524 A1 * | 4/2012 | Fridman et al. | 435/2 |
| 2012/0156091 A1 * | 6/2012 | Fridman et al. | 422/22 |
| 2012/0156341 A1 * | 6/2012 | Rasanayagam et al. | 426/234 |
| 2012/0183437 A1 * | 7/2012 | Keener et al. | 422/23 |
| 2012/0187841 A1 | 7/2012 | Kindel et al. | |
| 2012/0259270 A1 | 10/2012 | Wandke et al. | |
| 2013/0022514 A1 | 1/2013 | Morfill et al. | |
| 2013/0053761 A1 * | 2/2013 | Morfill et al. | 604/23 |
| 2013/0053762 A1 | 2/2013 | Rontal et al. | |
| 2013/0072860 A1 * | 3/2013 | Watson | A61M 16/12 604/23 |
| 2013/0134878 A1 | 5/2013 | Selwyn | |
| 2013/0199540 A1 | 8/2013 | Buske | |
| 2013/0259741 A1 * | 10/2013 | Lanz | 422/4 |
| 2014/0000810 A1 | 1/2014 | Franklin et al. | |

FOREIGN PATENT DOCUMENTS

| | | |
|---|---|---|
| WO | WO 2007/124910 A2 | 11/2007 |
| WO | WO 2010/107722 A1 | 9/2010 |
| WO | WO 2011/055368 A2 | 5/2011 |
| WO | WO 2011/055369 A2 | 5/2011 |
| WO | WO 2011/076193 A1 | 6/2011 |
| WO | WO 2012/106735 A2 | 8/2012 |
| WO | WO 2012/153332 A2 | 11/2012 |
| WO | WO 2013/101673 A1 | 7/2013 |

OTHER PUBLICATIONS

Written Opinion of the International Searching Authority issued Apr. 14, 2014 for Appl. No. PCT/US2013/074437, 4 pages.

Misra et al., "Nonthermal Plasma Inactivation of Food-Borne Pathogens," *School of Food Science and Environmental Health at Dublin Institute of Technology*, 32 pages (2011).

Dumé, Belle, "Cold Plasmas Destroy Bacteria," article, [online], [retrieved on Jan. 5, 2007], Retrieved from the PhysicsWeb website using Internet <URL:http://physicsweb.org/articles/news7/4/19>.

Gould, Phillip and Eyler, Edward, "Ultracold Plasmas Come of Age," article [online], [retrieved on Jan. 5, 2007], Retrieved from the PhysicsWeb website using Internet <URL:http://physicsweb.org/articles/world/14/3/3>.

Schultz, James, "Cold Plasma Ignites Hot Applications," article, [online], [retrieved on Jan. 5, 2007], Retrieved from the Old Dominion University website using Internet <URL:http://www.odu.edu/ao/instadv/quest/coldplasma.html>.

Lamba, Bikram, "Advent of Cold Plasma," article, [online], [retrieved on Jan. 5, 2007], Retrieved from the PhysOrg.com website using Internet <URL:http/www.physorg.com/printnews.php?newsid=6688>.

Book of Abstracts, 3rd International Conference on Plasma Medicine (ICPM-3), Sep. 19-24, 2010, International Society for Plasma Medicine.

International Search Report issued Aug. 6, 2008 for Appl. No. PCT/US2008/061240, 1 page.

Written Opinion of International Searching Authority issued Aug. 6, 2008 for Appl. No. PCT/US2008/061240, 6 pages.

Extended European Search Report issued Feb. 8, 2012 for European Patent Appl. No. EP08746627.2, 7 pages.

Pointu et al., "Nitrogen Atmospheric Pressure Post Discharges for Surface Biological Decontamination inside Small Diameter Tubes," *Plasma Process. Polym.* 5:559-568, WILEY-VCH Verlag GmbH & Co. KGaA, Weinheim (2008).

Chakravarthy et al., "Cold Spark Discharge Plasma Treatment of Inflammatory Bowel Disease in an Animal Model of Ulcerative Colitis," *Plasma Medicine* (1)1:3-19, Begell House, Inc. (2011).

Fridman et al., "Comparison of Direct and Indirect Effects of Non-Thermal Atmospheric-Pressure Plasma on Bacteria," *Plasma Processl Polym.*, 4, 370-375, 6 pages, WILEY-VCH Verlag GmbH & Co. KGaA, Weinheim (2007).

Alexander Fridman, "Plasma Chemistry," pp. 263-271, Cambridge University Press, 2008, 9 pages.

O'Connell et al., "The role of the relative voltage and phase for frequency coupling in a dual-frequency capacitively coupled plasma," *Applied Physics Letters*, 93 081502, 3 pages, American Institute of Physics (Aug. 25, 2008).

(56) References Cited

OTHER PUBLICATIONS

Nie et al., "A two-dimensional cold atmospheric plasma jet array for uniform treatment of large-area surfaces for plasma medicine," New Journal of Physics, 11 115015, 14 pages, IOP Publishing Ltd and Deutsche Physikalische Gesellschaft (2009).

Pompl et al., "The effect of low-temperature plasma on bacteria as observed by repeated AFM imaging," New Journal of Physics, 11 115023, 11 pages, IOP Publishing Ltd and Deutsche Physikalische Gesellschaft (Nov. 26, 2009).

Walsh et al., "Three distinct modes in a cold atmospheric pressure plasma jet," J. Phys. D.: Appl. Phys. 43 075201, 14 pages, IOP Publishing Ltd (Feb. 3, 2010).

Ricci et al., "The effect of stochastic electrical noise on hard-to-heal wounds," Journal of Wound Care, 8 pages, 19:3 Mark Allen Publishing Ltd ( Mar. 2010).

U.S. Appl. No. 61/485,747, filed May 13, 2011, inventor Thomas J. Sheperak, 14 pages.

Liu et al., "Sub-60°C. atmospheric helium-water plasma jets: modes, electron heating and downstream reaction chemistry," J. Phys. D: Appl. Phys. 44 345203, 13 pages, IOP Publishing Ltd. (Aug. 11, 2011).

Pei et al., "Inactivation of a 25.5 µm Enterococcus faecalis biofilm by a room-temperature, battery-operated, handheld air plasma jet," J. Phys. D. Appi. Phys., 45 165205, 5 pages, IOP Publishing Ltd (Apr. 4, 2012).

Walsh et al., "Chaos in atmospheric-pressure plasma jets," Plasma Sources Sci. Technol., 21 034008, 8 pages, IOP Publishing Ltd (May 2, 2012).

Banu, et al., "Cold Plasma as a Novel Food Processing Technology," International Journal of Emerging trends in Engineering and Development, Issue 2, vol. 4, ISSN 2249-6149, pp. 803-818, 16 pages. (May 2012).

Dobrynin, et al., "Live Pig Skin Tissue and Wound Toxicity of Cold Plasma Treatment," Plasma Medicine, 1(1):93-108, 16 pages, Begell House, Inc. (2011).

Fernández, et al., "The inactivation of Salmonella by cold atmosphere plasma treatment," Food Research International, 45:2, 678-684, 7 pages, Elsevier Ltd. (Mar. 2012).

Tien, et al., "The Bilayer Lipid Membrane (BLM) Under Electrical Fields," IEEE Transactions on Dielectrics and Electrical Institute, 10:5, 717-727, 11 pages (Oct. 2003).

Jayaram, et al.., "Optimization of Electroporation Waveforms for Cell Sterilization," IEEE Transactions on Industry Applications, 40:6, 1489-1497, 9 pages (2004).

Fridman, et al., "Use of Non-Thermal Atmospheric Pressure Plasma Discharge for Coagulation and Sterilization of Surface Wounds," IEEE International Conference on Plasma Science, Abstract, p. 257, 1 page (Jun. 2005).

Fridman, et al., "Use of Non-Thermal Atmospheric Pressure Plasma Discharge for Coagulation and Sterilization of Surface Wounds," 6 pages (Jun. 2005).

Fridman, et al., "Blood Coagulation and Living Tissue Sterilization by Floating-Electrode Dielectric Barrier Discharge in Air," Plasma Chem Plasma Process, 26: 425-442, 18 pages, Springer Science Business Media, Inc. (2006).

Gurol, et al., "Low Temperature Plasma for decontamination of E. coli in milk," International Journal of Food Microbiology, 157: 1-5, 5 pages, Elsevier B.V. (Jun. 2012).

Lado, et al., "Alternative food-preservation technologies: efficacy and mechanisms," Microbes and Infection, 4: 433-440 8 pages, Elsevier SAS (2002).

Leduc, et al., "Cell permeabilization using a non-thermal plasma," New Journal of Physics, 11: 115021, 12 pages, IOP Publishing Ltd and Deutsche Physikalische Gesellschaft (2009).

Machado, et al., "Moderate electric fields can inactivate Escherichia coli at room temperature," Journal of Food Engineering, 96: 520-527, 8 pages, Elsevier Ltd. (2009).

Li, et al., "Optimizing the distance for bacterial treatment using surface micro-discharge plasma," New Journal of Physics, 14: 023058, 11 pages, IOP Publishing Ltd and Deutsche Physikalische Gesellschaft (Feb. 2012).

Morfill, et al., "Nosocomial infections—a new approach towards preventive medicine using plasmas," New Journal of Physics, 11: 115019, 10 pages, IOP Publishing Ltd and Deutsche Physikalische Gesellschaft (2009).

Nian, et al., "Decontamination of Salmonella on Sliced Fruits and Vegetables Surfaces using a Direct-Current, Atmospheric-Pressure Cold Plasma," IEEE International Conference on Plasma Science, p. 1, 1 page (Jun. 2011).

Toepfl, et al., "High intensity pulsed electric fields applied for food preservation," Chemical Engineering and Processing, 46: 537-546, 10 pages, Elsevier B.V. (2007).

\* cited by examiner

METHOD AND APPARATUS FOR COLD PLASMA FOOD CONTACT SURFACE SANITATION

CROSS REFERENCE TO RELATED APPLICATIONS

This application claims the benefit of U.S. Provisional Application No. 61/735,804, filed Dec. 11, 2012 and entitled "Method and Apparatus for Cold Plasma Food Contact Surface Sanitation," which is incorporated herein by reference in its entirety.

BACKGROUND

1. Field of the Art

The present invention relates to devices and methods for food contact surface sanitation and, more particularly, to such devices that are cold plasma based and methods for using same.

2. Background Art

Microbiological pathogens continuously pose a problem in the food processing industry from both a safety and a cost standpoint. When introduced onto food contact surfaces in food production systems, such as food transferring conveyors, they pose a significant safety risk to the food supply and ultimately the consumers. These microbes are not endemic to food processing plants, but are usually brought into the facilities by contaminated agricultural products or poor practices among staff and visitors. A single item containing a pathogenic microorganism can contaminate large volumes of food products by transferring those microbes to food transport surfaces, which in turn transfer the microbes to other foods. Since these surfaces are cleaned only at set intervals, or when quality control tests indicate a problem, there is a substantial risk of large batch contamination from a very small inoculant.

Food allergens can pose a similar risk to individuals with specific food sensitivities. Food allergens are generally proteinaceous and may be easily transferred from one food product to another on food transport surfaces and processing machinery. Since proteins readily adhere to surfaces, they can be difficult to eliminate and often must be denatured by heat or chemical means.

People and animals can suffer from serious illness or even death when exposed to food pathogens or allergens. Because of this, numerous regulations for testing, cleaning, and maintenance are enforced in food production facilities to help reduce or eliminate pathogens and contaminants, thereby protecting the consumer. Effective food contact surface and processing equipment sanitation is one key to a safe food supply. This process is costly, reduces plant productivity, and requires dozens of man-hours to complete, often requiring partial disassembly of complex machinery. Methods currently being used to sanitize food contact surfaces include chemical, high temperature, ultraviolet (UV) and gamma irradiation.

Recently, non-thermal or "cold" plasmas (ionized gases) have gained attention for their ability to kill a wide variety of microorganisms, including foodborne pathogens, at high log reductions (a log reduction is a reduction by a factor of a power of 10, e.g., a log 2 reduction is a reduction by a factor of 100), with short exposure times. Cold plasmas have also been shown to denature proteins, which may reduce or eliminate allergens on food contact surfaces.

BRIEF SUMMARY OF THE INVENTION

What is needed is the ability to apply these "cold plasmas" in a food processing context to provide improved food safety. What is further needed is the ability to generate large volumes of cold plasma at the interface with food contact surfaces in a sale and of manner in a food processing plant. In particular, what is needed is a plasma treatment module for the continual sanitation of food transport surfaces while these surfaces remain in operation. This Will greatly improve food safety for consumers and at the same time improve throughput and profitability for producers and manufacturers.

An embodiment is described of an apparatus that can kill or reduce a microbiological pathogen or denatures a protein associated with food, in a food processing system. The apparatus includes a cold plasma device that is configured to direct a cold plasma at a target substrate over an effective area for an effective amount of time.

A further embodiment is described of a method of killing or reducing a microbiological pathogen, or denaturing a protein associated with food, in a food processing system. The method includes contacting a target substrate with a cold plasma over an effective area for an effective amount of time.

BRIEF DESCRIPTION OF THE DRAWINGS/FIGURES

FIG. 1A shows the control condition and FIG. 1B shows the growth inhibition zone after being treated with cold plasma in accordance with embodiments of the present invention.

FIG. 4A illustrates an untreated control sample and FIG. 4B illustrates treatment for 30 seconds, in accordance with embodiments of the present invention.

DETAILED DESCRIPTION OF THE INVENTION

Figure 1:
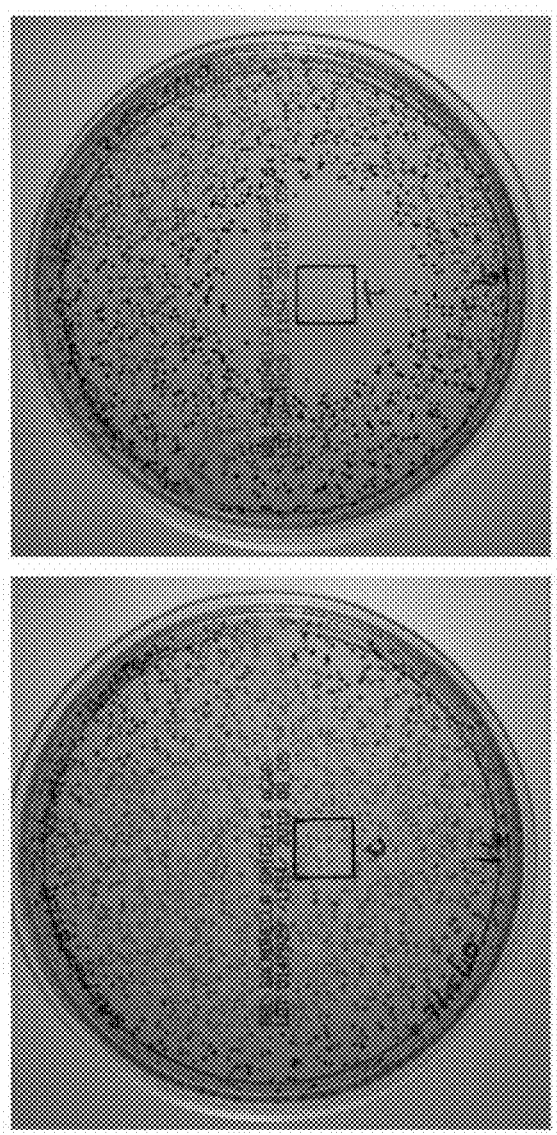
FIGS. 1A and 1B illustrate *Salmonella* cultured on *Salmonella Shigella* (SS) agar seeded at $10^3$ CFU/ml (colony-forming units per milliliter).

Cold temperature plasmas have attracted a great deal of enthusiasm and interest by virtue of their provision of plasmas at relatively low gas temperatures. The provision of plasmas at such a temperature is of interest to a variety of applications, including wound healing, anti-bacterial processes, various other medical therapies and sterilization. Embodiments of the present invention are directed to food preparation applications.

An objective of certain embodiments in the present disclosure is to develop a cold plasma array that provides a chemical free, dry, non-thermal, environmentally friendly, flexible, fast and effective antimicrobial solution for improved food safety, nutrition, and health. Such embodiments may improve the safety of foods moving through any processing facility that uses belts and conveyors, may improve throughput and efficiency of food processing facilities by reducing offline cleaning time, may reduce food recalls due to microbial contamination, reduce allergen cross-contamination, and may reduce the amount of chemicals and water used in the cleaning process for improved environmental health and sustainability.

The novel approach described in various embodiments allows for the low cost construction of very large DBD plasma delivery devices that can be assembled into large arrays and driven by a unified power source. These large arrays can be retrofitted to the underside of existing food transport conveyor systems to continually treat the belt surface when it is devoid of food products. By treating the surface after it has delivered its load and prior to pick up of the next load, the ability to spread pathogens from a single contaminated item to a large batch of food product will be greatly curtailed. This will significantly reduce offline cleaning times of direct food contact surfaces and improve the overall safety of the food supply delivered to consumers. Also, surfaces that may be too sensitive for existing cleaning techniques (i.e., UV, thermal, chemical, etc.) could be treated with cold plasma for sanitizing purposes. It is expected that allergens and toxins would be denatured by the same plasma treatment array, thereby contributing further safety and efficiency improvements.

Food Transport Surface Sanitation

As noted above, surface sanitation is a vital process and a serious concern in the food processing industry. Companies spend millions of dollars every year to make sure that their food contact surfaces remain clean of harmful microorganisms such as bacteria, mold, and yeast. The current methods, although effective, have many problems. Thermal and autoclaving sanitizing methods will not work with polymer-like materials because of their low resistivity to heat. These methods are also time-consuming and there are significant size limitations on the equipment that can be placed inside of a thermal sterilizer. Various chemical reagents are utilized such as ethylene oxide (ETO), and reducing agents such as chlorine, and hydrogen peroxide. However, these chemical modes of sanitation can be harmful to humans because of their toxicity and may require substantial volumes of rinse water. Ultraviolet (UV) and gamma irradiation require a relatively long exposure time and can have limited effectiveness on certain pathogens and on porous surfaces. These methods are also mutagenic and must be carried out in specialized containment areas to protect workers from exposure. With these potential problems and dangers, a better method of sanitation/disinfection/sterilization could have a dramatic impact on the food processing industry. Cold plasma technology can address all of these concerns and limitations.

Allergens on Food Transport Surfaces

In addition to foodborne illnesses, each year millions of people suffer from allergic reactions caused by foods. Although most of these reactions have minor symptoms, it is estimated 150 to 200 Americans die each year due to severe anaphylactic allergic reactions to food allergens. In 2004, the U.S. Congress passed the Food Allergen Labeling and Consumer Protection Act of 2004 (FALCPA). This law helped the allergen-sensitive consumer identify offending products to their condition. In addition, many food manufacturers voluntarily put warning labels on products that may be cross contaminated by food containing possible allergens. Currently, the only methods available to destroy or denature proteins are by treating the contaminated surface with either extremely acidic agents or high temperatures.

Some of the common food allergies include milk, eggs, fish, peanuts, wheat, tree nuts, and soybeans. Allergic reactions to food products are caused by the body's immune system responding to the allergen as a threat. Typically, a protein within, or introduced to the surface of, the adverse food sparks an immune response. For instance, peanuts have at least 8 different proteins that can cause allergic reactions (Ara h1-Ara h8). Research suggests that cold plasmas can alter the structure of proteins and inactivate them. In particular, cold plasmas can inactivate proteins that are difficult to address with conventional means, such as prions and bacterial toxins, both of which have a direct impact on food processing. If the binding sites on the food allergen protein which are recognized by the immune system are altered substantially, the allergen may be rendered harmless. The high risk of cross-contamination on food contact surfaces, coupled with the fact that more and more people suffer from one or more food allergies, has made this a growing problem in the industry. Besides improving the sanitation/disinfection/sterilization processes, the incorporation of cold plasma into the food manufacturing industry could also substantially decrease allergen cross-contamination.

Effects of Cold Plasma on Microbes and Proteins

The first reports of successful microbial destruction with cold plasma date from 1996, and in the last decade, a substantial number of additional publications have emerged to further support these early reports. These reported tests have been performed on a wide array of substrates including agar dishes, laboratory animals, food products, plastics that are representative of food transport surfaces, and even within small diameter tubes that have utility for medical and food processing safety. Reported log reductions vary greatly (log 3 to greater than log 7) due to different plasma devices used; dielectric barrier discharge (DBD) versus atmospheric pressure plasma jet (APPJ), different electrical signatures employed in the plasma generation, different exposure times (sub-second to several minutes), different strains tested, and different substrates tested.

Additionally, recent publications suggest plasma can denature proteins, even proteins that are difficult to eliminate and have an impact on food safety, such as prions and bacterial endotoxin. Precisely how plasma actually achieves sanitation and protein modification is not yet fully understood and is likely to be a combination of several mechanisms of action. Physical mechanisms (such as electroporation, charged particle bombardment and UV), chemical mechanisms reactive species, free radicals) and biological mechanisms (cellular processes such as deoxyribonucleic acid (DNA) and cell membrane damage) all appear to play a role in the inactivation of bacteria, and the relative contribution of each likely varies between plasma delivery systems, contributing to the lack of consensus.

Barriers to Deployment of Cold Plasmas on an Industrial Scale

The cold plasma generators generally described in the plasma literature and prior art are capable of generating only small plumes of non-thermal plasmas that contact very small areas, on the order of 1-2 linear cm or a few cm square at maximum. As the size of the generating electrode(s) are scaled up, the amount of energy required to effectively generate a plasma discharge increases, and this in turn drives up the plasma temperatures. Therefore, while destructive effects on microbes and proteins have been demonstrated in the literature with non-thermal plasmas on a small scale, attempts to scale these systems to treat the larger areas necessary for industrial level treatment generally fail because the plasma become increasingly thermal. Eventually, the thermal content of the plasma detracts from the intended application of a non-thermal plasma to a sensitive heat sensitive surface, animal, or food product.

Cold plasma sources in the plasma literature are typically single frequency plasmas. Single frequency plasmas suffer from an inability to scale in size, and are thereby limited in their area of treatment to small surfaces, such as surfaces with an associated size of approximately 3 sq. cm. In the case of DBD plasmas, in order for the plasma arc to initiate, a ground potential must be present on the treatment to target. In the case of non-conductive treatment targets, it can be difficult to initiate plasma generation. Placing a ground on the opposing side of the treatment surface can be an effective work around, but single frequency plasma is limited in material thickness and distance between electrodes. In addition, single frequency plasmas are unable to initiate on thick dielectric treatment surfaces, even were a ground plane available to direct the cold plasma through the intervening treatment surface.

Multi-Frequency Harmonic-Rich Cold Plasma

One method of overcoming the above limitations of plasma surface area generation and penetration is to utilize a multi-frequency harmonic-rich cold plasma (MFHCP). The MFHCP cold plasma sources of the present disclosure can be configured to provide large treatment areas, as well as good penetration of the treatment surface. MFHCP cold plasma sources incorporate the power system and associated applicators is described in U.S. Provisional Patent Application No. 60/913,369, U.S. Non-provisional application Ser. No. 12/038,159 (that has issued as U.S. Pat. No. 7,633,231) and the subsequent continuation applications (collectively "the '369 application family"), and the cold plasma high voltage power supply described in U.S. patent application Ser. No. 13/620,118 and U.S. Provisional Patent Application No. 61/535,250, which are incorporated herein by reference. Inventors consider the capability of providing multi-frequency rich harmonic cold plasma (MFHCP) over an arbitrary length to be an important contribution to applications such as those described herein. MFHCP results, in part, from the use of a power supply that provides electrical energy across a multitude of frequencies to excite the ions in the as (e.g., air in this case). Conventional cold plasmas typically direct electrical energy at a single frequency and are thereby limited in their flexibility while maintaining the temperature of the cold plasma. In contrast, by directing the electrical energy across a multitude of frequencies in an MFHCP cold plasma, scalable cold plasma solutions can result, including the ability to support cold plasmas of an arbitrary length.

The MFHCP device includes an RF tuning network that is within one single power supply, as described in U.S. Provisional Patent Application No. 60/913,369, U.S. Non-provisional application Ser. No. 12/038,159 (that has issued as U.S. Pat. No. 7,633,231) and the subsequent continuation applications (collectively "the '369 application family"), which are incorporated herein by reference. Each universal power supply contains a low-voltage power supply, a high-voltage coil, and a capacitor that works to produce a high voltage RF signal. Each harmonic RF signal is transferred to a cold plasma device through a protected cable that allows the electrical energy to be transferred without any substantial corona discharge energy loss.

Figure 4:
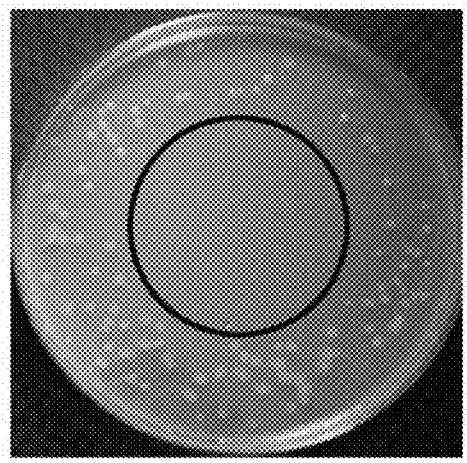
FIGS. 4A and 4B illustrate a test of a dielectric barrier discharge DBD) cold plasma on *E. coli* seeded at $10^7$ CFU/ml.
Figure 4:
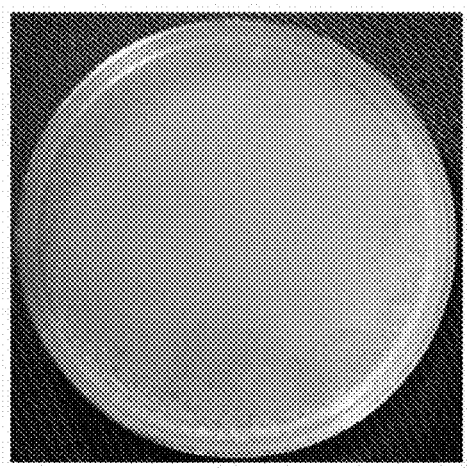

In an embodiment of the present invention, a DBD electrode powered by the MFHCP power supply provided a cool, evenly-distributed, plasma over electrode lengths in excess of 244 cm, or eight (8) linear feet. With electrodes of the lengths described in the prior art it is impractical to treat food transport surfaces in situ. For perspective, most previous DBD plasma electrodes are on the order of 1-2 cm, and the prior art known at the time of filing does not disclose any DBD plasma electrodes capable of producing cold plasma plumes in excess of approximately 3 sq. cm. In particular, the prior art does not disclose any DBD plasma electrodes that are suitable for large scale use in the food processing industry. Pilot testing of these extended cold plasma DBD electrodes have again confirmed the ability of MFHCP to destroy a wide array of microbes at high log reductions with 30 second exposure times or less (FIG. 4). The local kill effect happens very quickly (within a few seconds) under the footprint of the electrode, but the longer the electrode is active, the greater the kill area outside of the electrode footprint. This effect outside of the electrode footprint improves the spacing requirements between electrodes in a large system array designed to treat a moving food transport conveyor, in accordance with an embodiment of the present invention.

The DBD plasma-generating devices described in embodiments of this invention are generally referred to as "electrodes" or "DBD electrodes" in this application. The electrodes can be provided in various shapes that are appropriate to the treatment surface. For example, a cylindrical shaped, polygonal shaped, or planar shaped electrode may be an embodiment suitable for a given application. However, a cylindrical-shaped electrode is merely exemplary, and other applicable electrodes appropriate to a particular application are within the scope of the present disclosure. In addition, either a single, or two or more DBD electrodes may be mounted in close proximity (defined as the maximum distance to achieve a plasma arch to the treatment surface at the applied voltage level and frequency) to the food contact surface. For food contact surfaces that are ungrounded, and therefore are incapable of acting as ground for the DBD plasma, a separate carrier designed to hold grounding element(s) can be mounted to the DBD electrode carrier assembly. These grounding element(s) would be located parallel with and adjacent to each of the DBD electrodes. These ground elements may be on the opposite side of the target surface or adjacent to and substantially coplanar with the plasma generating electrodes such that the plasma is generated parallel to the treatment surface rather than perpendicular to it. In a similar manner to the electrode, the grounding element(s) may take on any shape appropriate to a particular application. For example, grounding element(s) may take on a planar, rod, circular, or conical shapes. The two assemblies, the DBD carrier and the grounding carrier, of the device can be mounted on an adjustable support bed that is placed on either side of the food contact surface allowing the contact surface to reside within the optimum treatment zone for the DBD device.

In addition to DBD electrode based embodiments, one or an array of atmospheric pressure plasma jet (APPS) based embodiments may also be configured to provide sufficiently large cold plasma plumes for a given particular application. The APPJ-based cold plasma sources also incorporate the power system and associated applicators is described in U.S. Provisional Patent Application No. 60/913,369, U.S. Non-provisional application Ser. No. 12/038,159 (that has issued as U.S. Pat. No. 7,633,231) and the subsequent continuation applications (collectively "the '369 application family"), and the cold plasma high voltage power supply described in U.S. patent application Ser. No. 13/620,118 and U.S. Provisional Patent Application No. 61/535,250, which we incorporated herein by reference.

Figure 2:
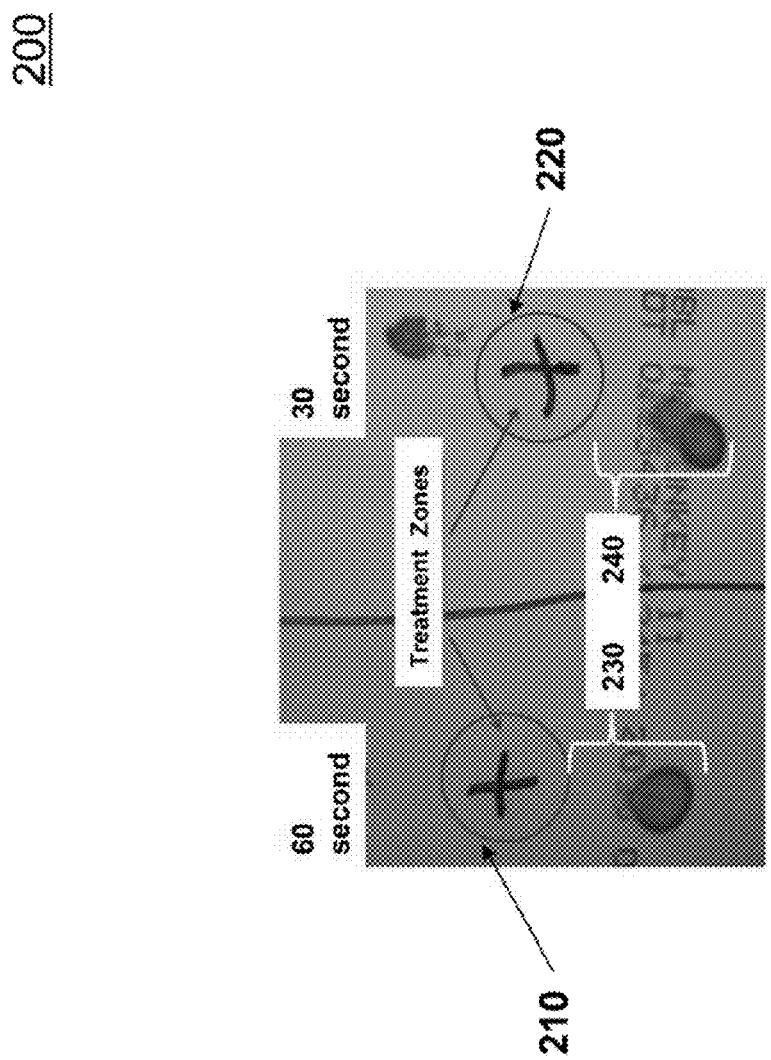
FIG. 2 illustrates an *E. coli* (0157:H7) exposure test, in accordance with embodiments of the present invention.

In terms of efficacy, the MFHCP device has been shown to destroy *Escherichia coli* (ATCC#: 25922), *Acinetobacter baumannii* (ATCC#: BAA-1605), *Micrococcus luteus* (ATCC#: 4698), *Pseudomonas aeruginosa* (ATCC#: 27853), *Staphylococcus aureus* (ATCC#: 6538) and Methicillin-resistant *Staphylococcus aureus*; MRSA (ATCC#: 33592), *Serratia marcescens* (ATCC#: 13880), as well as fungus strains such as *Candida albicans* (ATCC#: 10231). A pilot study of foodborne pathogens, including *E. coli* (0157:H7) and *Salmonella enterititis*, treated with MFHCP demonstrated a very high level of destruction (log 3 to log 7, depending upon test parameters) with short exposure times of 30-60 seconds (FIGS. 1 and 2). Additionally, in a second experiment, MFHCP was observed to prophylactically prevent the growth of *E. coli* (0157:H7) that was seeded on agar after plasma treatment (FIG. 3).

Exploring these results further, FIG. 1 illustrates the impact of MFHCP on *Salmonella* cultured on SS agar seeded at $10^3$ CFU/ml (colony-forming units per milliliter). FIG. 1A (left, photo) illustrates the untreated control sample, while FIG. 1B (right photo) was treated with MFHCP for 30 seconds. A log 3 reduction (i.e., reduction by 1000) was easily achieved. The plasma was applied only within the square marked "T" but created a zone of inhibition substantially larger than the diameter of the plasma plume.

FIG. 2 illustrates a preliminary *E. coli* (0157:H7) exposure test. Active bacteria appear pink when cultured on MacConkey agar. This was a very dense seeding challenge with an undiluted Kwik-Stik™ from Microbiologics Inc., seeding at greater than $10^7$ CFU/ml. FIG. 2 illustrates two treatment zones 210, 220 and untreated areas 230, 240. Two exposures of MFHCP were applied, a 30-second exposure and a 60-second exposure. On the left side of FIG. 2 are the 60-second exposure areas, namely the treatment zone 210 and the untreated area 230. On the right side of FIG. 2 are the 30-second exposure areas, namely the treatment zone 220 and untreated area 240. Within the treatment zones 210, 220, there is no growth evident after 24 hours following either a 30 or 60 second exposure. The 60 second exposure has a larger inhibition zone outside of the direct plasma contact area.

Figure 3:
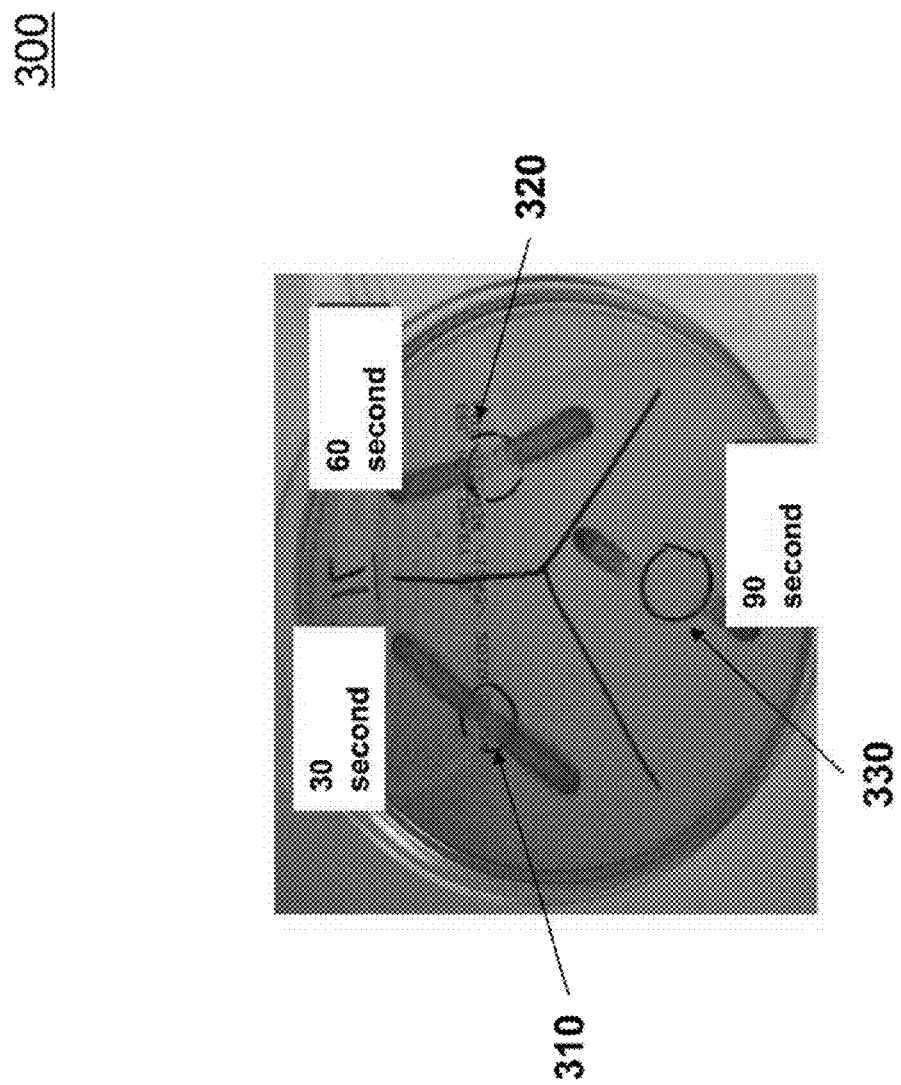
FIG. 3 illustrates the results of preliminary prophylactic surface treatments to inhibit pathogen growth (*E. coli*, 0157:H7), in accordance with embodiments of the present invention.

FIG. 3 illustrates the results of, prophylactic surface treatments to inhibit pathogen growth. The agar surface was treated with MFHCP for 30, 60, and 90 seconds prior to inoculation. Treatment sector 310 undergoes a 30-second pre-treatment, treatment sector 320 undergoes a 60-second pre-treatment, and treatment sector 330 undergoes a 90-second pre-treatment. After pre-treatment, the plate was set aside for 60 seconds and then a swab with a very dense inoculant (>$10^7$ CFU/ml) was run across each of the three treatment sectors 310, 320, and 330, respectively. There is a clear dose-response curve for the pretreated zones, with growth evident in the 30 and 60-second treatment areas, and a greater growth evident in the 30-second treatment area. Importantly, the 90 second pretreatment prevented the growth of any *E. coli* (0157) within the treatment zone.

FIGS. 4A and 4B illustrate a recent test of a MFHCP DBD plasma tested on *E. coli* seeded at $10^7$ CFU/ml and treated for 30 seconds. FIG. 4A (left figure) is the control sample, with bacterial confluence on the entire surface, while FIG. 4B (right figure) is treated for 30 seconds with a MFHCP DBD plasma. The circle on the right figure shows the approximate footprint of the electrode of the cold plasma DBD plasma. Complete sanitation occurs within the electrode footprint and >5 log reduction (greater than a 100,000 reduction) occurs in the margins of the plate.

Denaturing of Proteins

Figure 5:
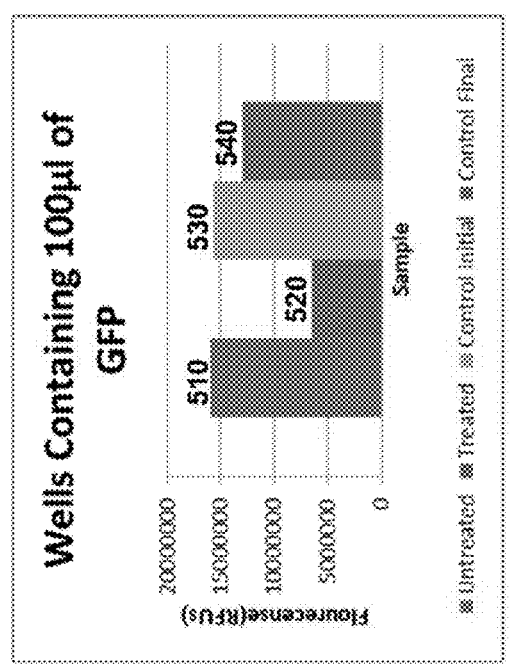
FIG. 5 illustrates green fluorescent protein (GFP) denaturing from a cold plasma treatment, in accordance with an embodiment of the present invention.

As discussed above, food allergens are primarily composed of specific proteins and are a major concern in the food industry. There are no published studies examining the effects of cold plasma treatments on specific allergens. However, there are encouraging studies demonstrating the ability of cold plasmas to denature proteins, including prions, which are notoriously difficult to destroy, as well as gram-negative bacterial endotoxin. When a protein is denatured, it undergoes a change of shape. If this shape change occurs at specific binding sites, important enzymes and immune related histamines may be unable to bind to, or recognize, the protein. FIG. 5 shows the results of a preliminary test indicating that cold plasma technology has the ability to denature proteins. A test was conducted using a green fluorescent protein (GFP) that has a natural fluorescence. If the protein is denatured, it loses its fluorescence, which is easy to quantify with standard spectral techniques. Ten 100 µliter samples of GFP were plated into wells and treated for 30 seconds with a cold plasma. The GFP fluorescence was measured using a spectrophotometer, before and after the treatment. There are four types of samples illustrated in FIG. 5. The first set 510 of samples are untreated samples with a measured fluorescence of 15,000,000 relative fluorescence units (RFU). The second set 520 of samples are cold plasma treated samples with a measured fluorescence of approximately 5,000,000 relative fluorescence units (RFU). The third set 530 of samples are the initial control samples with a measured fluorescence of 15,000,000 relative fluorescence units (RFU). Finally, the fourth set 540 of samples are the control samples exposed to atmospheric conditions for a similar time as second set 520 was exposed to cold plasma, with a measured fluorescence of approximately 13,000,000 relative fluorescence units (RFU). The initial results show a dear decrease in the protein's fluorescence after cold plasma treatment and confirm that cold plasma may be useful for the destruction of allergen proteins.

Food Processing Cold Plasma Device Development

Figure 6:
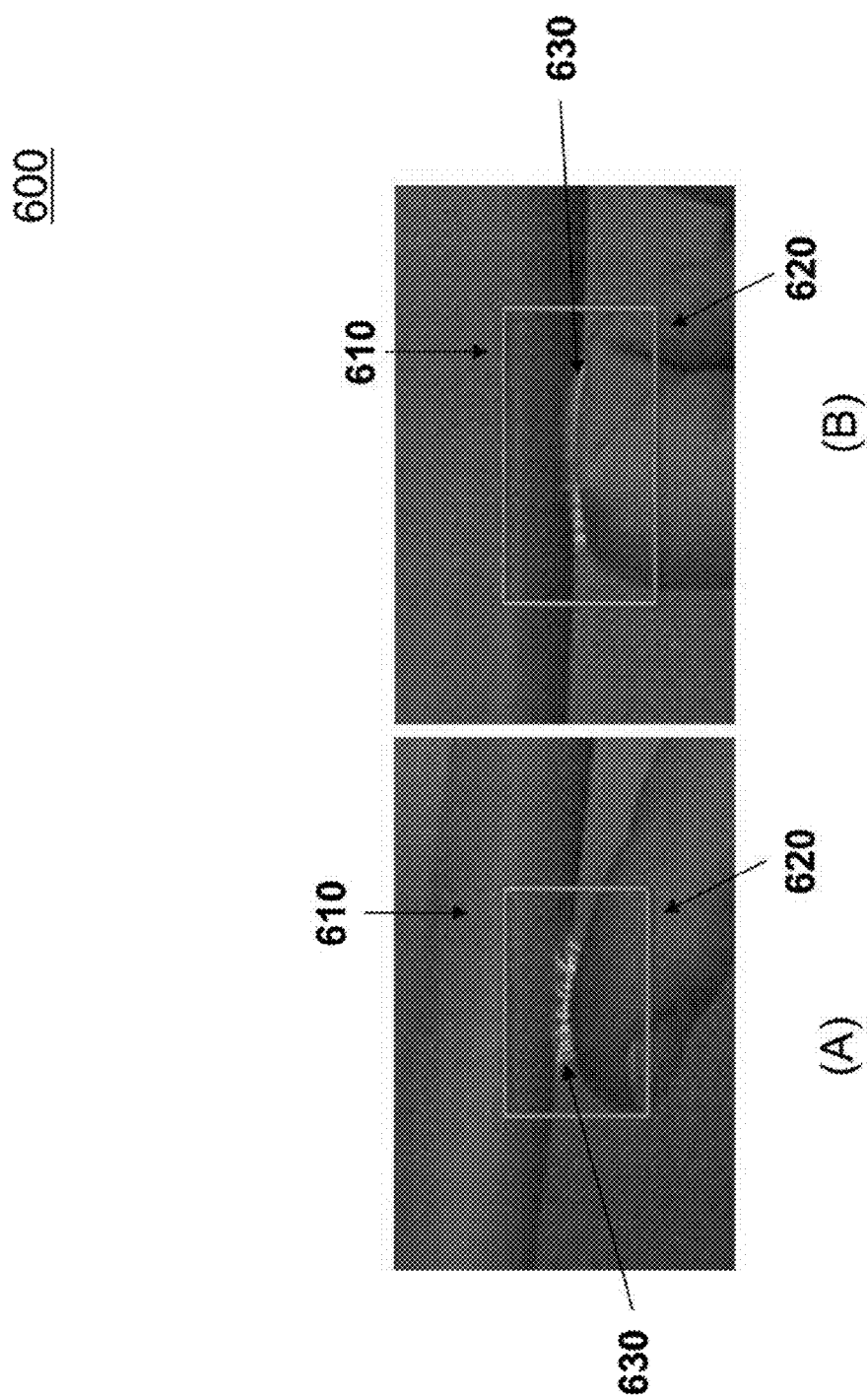
FIGS. 6A and 6B illustrate an exemplary embodiment of the cold plasma surface treatment DBD electrode, in accordance with an embodiment of the present invention.

As discussed above and demonstrated in FIG. 4, a MFHCP electrode device has been developed for the effective sanitation of surfaces, in accordance with an embodiment of the present invention. FIGS. 6A and 6B illustrate one of these devices generating a sustained plasma discharge between the electrode and a human finger, in order to demonstrate the non-thermal properties of this plasma. This electrode uses a simple and cost effective construction consisting of a length of metallic tubing shrouded in a dielectric coating. In this embodiment, a length of copper pipe 25 cm long forms the central electrode and a common heat shrink material is used as the dielectric covering. The dielectric barrier surface could be made of polytetrafluoroethylene (PTFE), delrin, polyethylene (PE), polypropylene (PP), quartz, glass, or other dielectric materials known to one skilled in the art. With any underlying electrode of sufficient capacitance to support the dielectric discharge.

FIGS. 6A and 6B illustrate a cold plasma surface treatment DBD electrode device, in accordance with an embodiment of the present invention. In this particular embodiment, the electrode is implemented in the form of a cylinder. FIGS. 6A and 6B illustrates DBD electrode device 610 in close proximity to a finger 620 and a resulting plasma 630. The illustration of FIGS. 6A and 6B show plasma auctioning around the margin and at the radius of curvature of the cylindrical electrode. As aforementioned, the cross section of the electrode does not need to be cylindrical, and could be polygonal or planar. Any conductive surface coated in an appropriate dielectric material will sustain a plasma discharge when powered by the MFHCP power supply.

Figure 7:
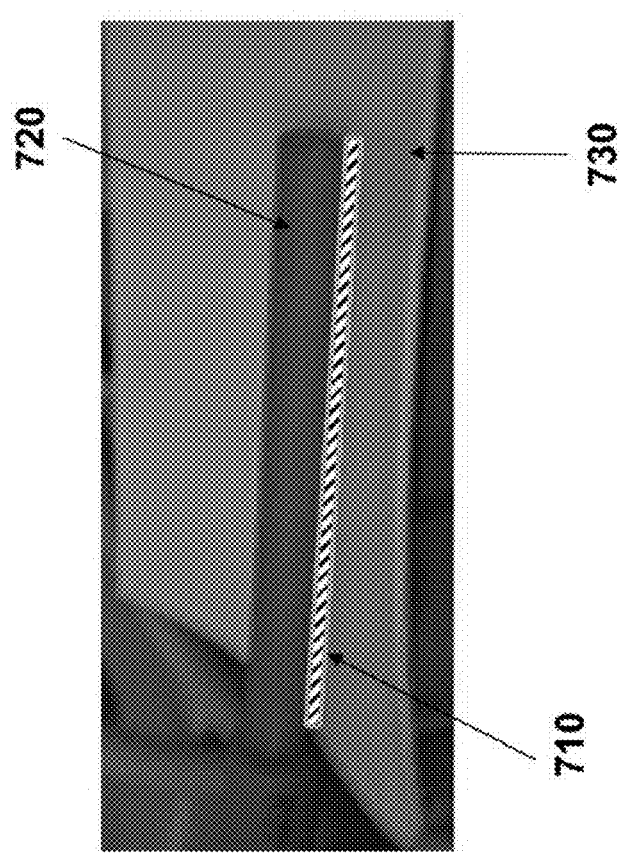
FIG. 7 illustrates an exemplary embodiment of the cold plasma corona on nitrile food conveyor surface, in accordance with an embodiment of the present invention.

FIG. 7 illustrates a DBD electrode 720 of approximately 25 cm in length placed in close proximity to a piece of food-grade nitrile belt material 730 (2.3 mm thick) and the resulting cold plasma 710 that is generated along the entire length of DBD electrode 720. In FIG. 7, cold plasma 710 between nitrile food conveyor surface 730 is a purple glow (shown as cross-hatched) that is visible along the full length of the 25 cm DBD electrode 720. One difficulty with DBD plasmas is getting them to arc to non-conductive surfaces, such as nitrile, vinyl, and rubbers. By placing a ground potential on the opposite side of a non-conductive surface, the MFHCP DBD is able to create plasma discharge along the entire length of the electrode, even when the ground potential is on the opposite side of a thick non-conductive surface.

Figure 8:
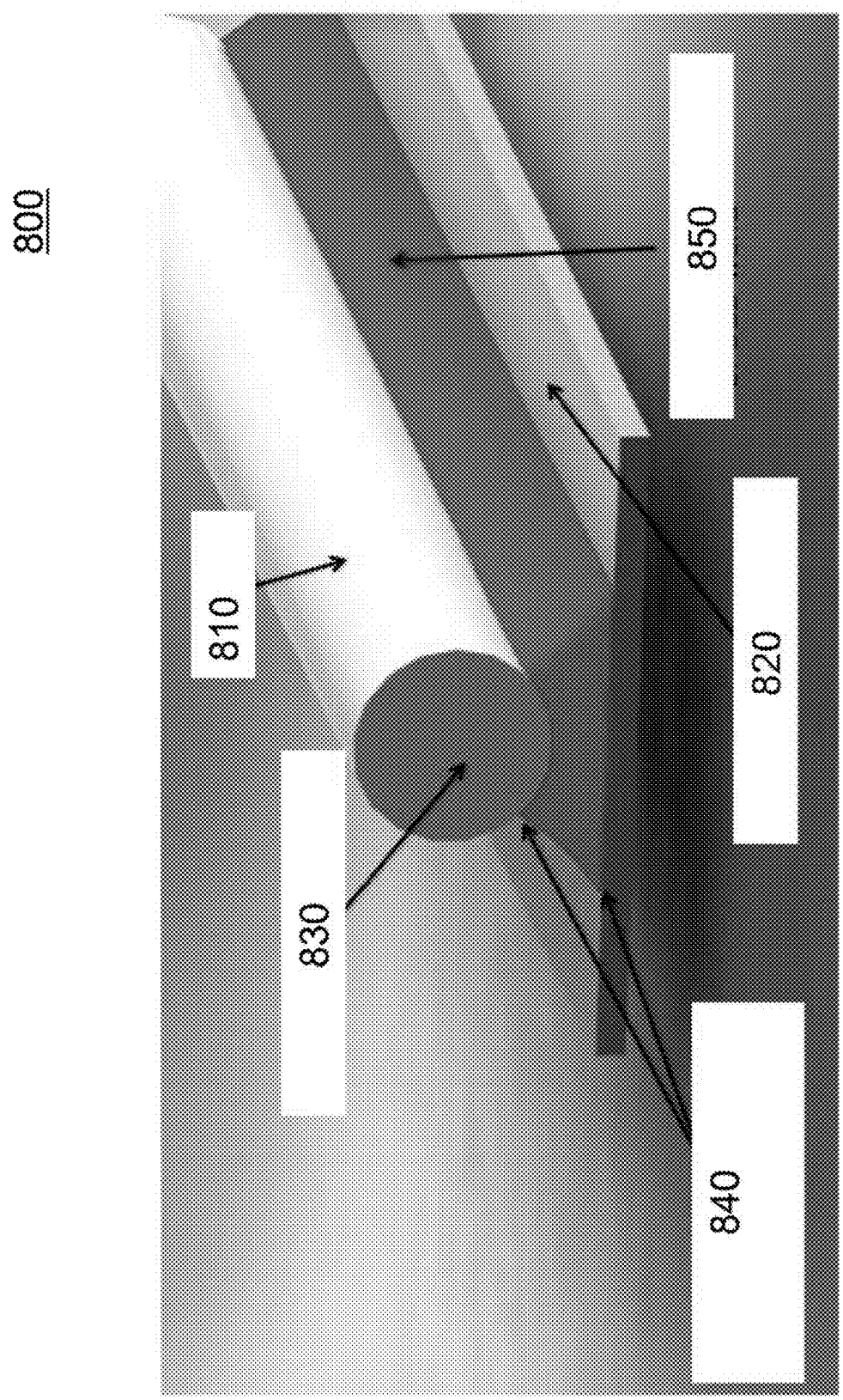
FIG. 8 illustrates a computer assisted design (CAD) model of cylindrical electrode applied to a flat substrate representative of a food transport belt, in accordance with an embodiment of the present invention.

The 25 cm length is exemplary of a length of DBD electrode suitable for use in applications such as the food processing industry. Longer lengths are also within the scope of embodiments within this disclosure. For example, MFHCP DBD electrodes have been tested that generate up to eight (8) linear feet of non-thermal plasma from a single power source. No upper bound is yet known as to the number of linear feet that can be generated when using a multi-frequency harmonic-rich power source. FIG. 8 represents this same phenomenon graphically for additional clarity, since photographing the plasma discharge and test set-up is challenging due to the low ambient light required to visualize the plasma corona.

The multi-frequency approach to plasma generation (as described in other patent applications by the inventors, such as U.S. Provisional Patent Application No. 60/913,369, U.S. Non-provisional application Ser. No. 12/038,159 (that has issued as U.S. Pat. No. 7,633,231) and the subsequent continuation applications (collectively "the '369 application family"), which are incorporated by reference) allows for the configuration of these large electrode sizes and thick dielectric material treatments because each frequency imparted to the electrode has a different breakdown potential to initiate a discharge. Therefore, discharges occur at different temporal and spatial locations along the entire electrode when it is charged to a desired voltage, generally between 10-25 kV, or approximately 15 kV, but may be as high as 50 kV. A cold plasma device utilizing this multi-frequency cold plasma technology could be used to sanitize/disinfect/sterilize food contact surfaces and food handling and packaging equipment without heat or hazardous chemicals.

FIG. 8 illustrates a cylindrical electrode 810 applied to a flat substrate 820 that is representative of a food transport belt, in accordance with an embodiment of the present invention. Note the mantle of plasma 850 generated along the margins of the electrode. Note also the plasma 840 along the radius curve of electrode 810 at its distal end 830.

The key element remaining for effective utilization of a DBD cold plasma in food processing facilities for the continuous sanitation of food transport surfaces is the provision of an array of plasma electrodes that can provide adequate contact time to achieve sanitation at the belt speeds normally encountered in food handling operations. As belt speed increases, the number of electrodes in an array will need to increase and the spacing between the electrodes may need to decrease.

As noted above, grounding elements may be used in conjunction with an MFHCP device. For example, in food transport belt embodiments and other embodiments, one or more grounding elements may be used in conjunction with the MFHCP devices to tailor the cold plasma plume to a particular shape, contour or region. Confining the cold plasma plume to a particular shape, contour or region ensures improved effectiveness by directing as much of the available cold plasma to the treatment region desired. Grounding elements may be composed of suitable materials that can influence the shape of the plasma plume, including conductive materials. In various embodiments, grounding elements may take on any shape appropriate to the desired treatment region. In one embodiment, the conveyor belt can be grounded and therefore can function as the ground for the DBD plasma generated by, the device.

Figure 9:
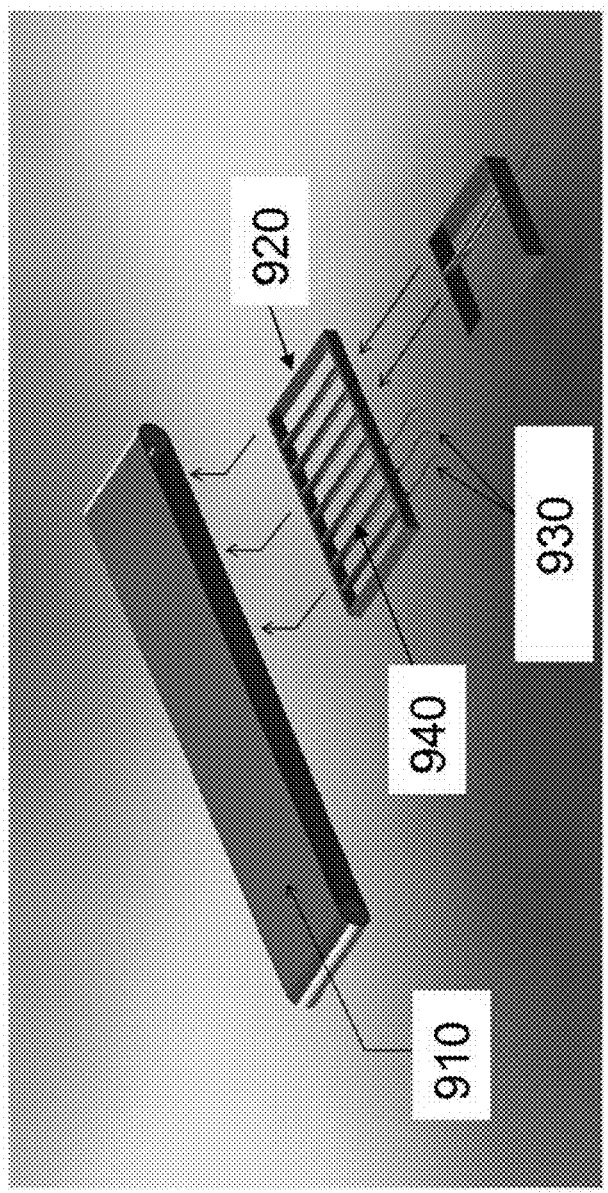
FIG. 9 illustrates a plasma sanitation module, in accordance with an embodiment of the present invention.

FIG. 9 illustrates a plasma sanitation module 900, in accordance with an embodiment of the present invention. The plasma sanitation module 900 may include a variable-speed conveyor system, e.g., food transport conveyor 910. The plasma sanitation module may further include a number (e.g., 40) of electrodes 940 of appropriate length (e.g., the full width of the conveyor, which is typically less than the 244 cm previously achieved with this device), similar to the one illustrated in FIG. 7. Each electrode 940 is coupled to its respective 930 RF/high voltage feed cable. Custom brackets and housings can be created for different manufacturers and styles of conveyor systems to allow the plasma sanitation module 900 to be retrofitted to existing processing equipment. The plasma sanitation module can be affixed by a bracket 920 to the underside of the food transport conveyor 910 so that the plasma does not interact directly with food products. This will sanitize the belt after it has unloaded a product at the end of its run, but before it returns to pick up additional food items. In this way, cross-contamination between one infected item and the next item to contact the belt in the same location will be eliminated. Such a plasma sanitation module 900 provides a substantial technical sanitation contribution, with a global impact on improved food safety.

Still referring to FIG. 9, the electrodes 940 in the plasma sanitation module 900 have been tested on bacterial samples, with excellent results. FIG. 9 illustrates how an array of these electrodes 940 may be assembled into a single housing that can be retrofitted to the underside of existing food transport conveyors. The power source (not shown) can be located remotely from the plasma sanitation module, as shown by the high voltage RF feed cables 930. The high voltage RF feed cables 930 are preferably powered by a MFHCP universal power supply as previously referenced.

In one embodiment, a frame is included that is designed to hold a single DBD element, or array of DBD elements, in close proximity to a food conveyor belt as illustrated in FIG. 9). In a particular embodiment, the framed DBD device would be located on the discharge end of the conveyor system, distal to the return idler or tail pulley, to allow time for bacterial kill and the dissipation of any reactive species, after bacterial reduction with the DBD plasma, before the conveyor again comes into contact with food items. The DBD device could be manufactured to meet the same design specification (e.g., consistent with the rail width of the conveyor belt system) as the particular food preparation surface (e.g., stationary food contact surface, food conveyor belt) that it is being paired to in order to ensure full coverage of the conveying surface. In applications with multiple/converging conveyors joined into a single system of production, a Dutchman, an intermediate bed, spur section, or food processing/transport systems utilizing crossovers, each belt could be supplied with its own cold plasma DBD food conveyor system belt sanitation device.

The MFHCP DBD food contact surface system sanitation device would contain a high voltage power supply and a dielectric barrier discharge surface that can be brought into direct contact with the underside of the food conveyor belt. In certain embodiments, the output signal would be a low duty cycle DC sine wave function with harmonic components similar to the devices described, for example, in U.S. patent application Ser. No. 13/620,118, which is incorporated by reference. Various embodiments may have similar form factors, with possible differences in the number of DBD units attached to the conveyor system.

Figure 10:
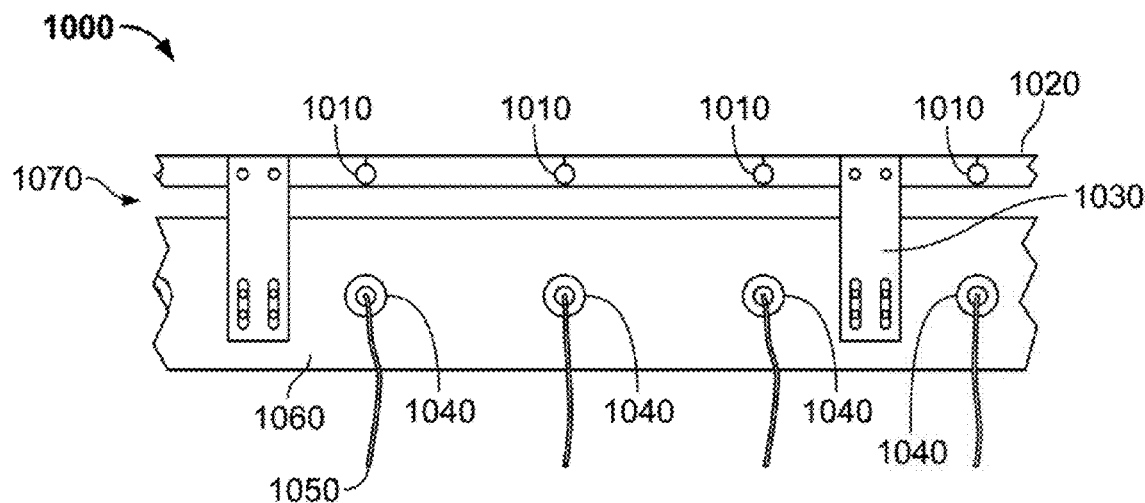
FIG. 10 illustrates a side view of a food conveyor DBD array with grounding assembly, in accordance with an embodiment of the present invention.

FIG. 10 illustrates a side view of a food conveyor DBD array highlighting the grounding element assembly which can be mounted to the DBD device carrier on an adjustable mount allowing for the entire rig to be adjusted to surround a food contact surface area 1070. Food contact surface area 1070 may be placed between grounding element assembly 1020 and DBD device carrier assembly 1060. A height adjustable ground bracket 1030 serves to provide the appropriate amount of separation between element assembly 1020 and DBD device carrier assembly 1060. Grounding element assembly 1020 includes a number of grounding elements 1010. Grounding elements 1010 may take any shape (e.g., rod) that is appropriate for the particular application. DBD device carrier assembly 1060 includes a number of DBD elements 1040. DBD elements 1040 may take any shape (e.g., cylindrical rod) that is appropriate for the particular application. Each DBD element 1040 is coupled to a high voltage feed cable 1050. Since the contact surface may be of a dielectric nature, the grounding element assembly allows for the plasma to be transferred to the target substrate.

The DBD device carrier could also be a combination device fitted with fluorescent bulbs that produce specific wavelengths of UV light to enhance the sterilization process. A parabolic mirror element could accompany the fluorescent bulbs mounted to the distal side of the carrier in order to more fully and evenly distribute the UV light, while reducing the loss of light to the surrounding area, as shown in FIG. 10 of the disclosure "Method and Apparatus for Dielectric Barrier Discharge Wand Cold Plasma Device," U.S. Provisional Application No. 61/747,828 filed Dec. 31, 2012.

Figure 11:
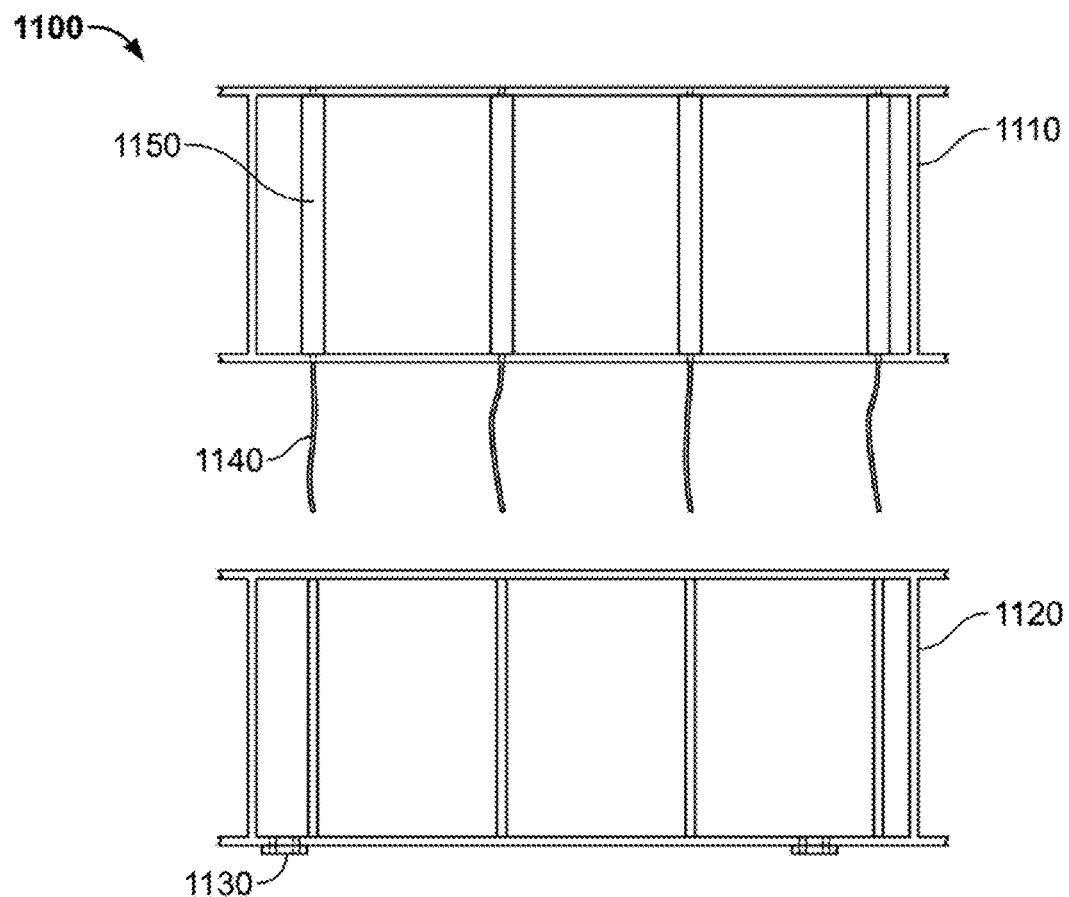
FIG. 11 illustrates a plan view of a two-part construction of the DBD array and the grounding rods, in accordance with an embodiment of the present invention.

FIG. 11 illustrates an embodiment of a DBD device 1100 having a two-part construction of a DBD array 1110 and a grounding element assembly 1120 that can be placed on the opposing side of the treatment substrate to facilitate the flow of the non thermal plasma to the food contact surface being sterilized or sanitized. DBD electrode array 1110 includes one or more DBD electrodes 1150, with each DBD electrode coupled to an RF feed cable 1140. Grounding element assembly 1120 includes one or more complementary grounding elements. Adjustable mounting bracket 1130 forms a portion of supporting assembly 1120.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method comprising:
    contacting a target substrate with a multi-frequency harmonic-rich cold plasma over an effective area for an effective amount of time to kill or reduce a microbiological pathogen, or denaturing a protein, in a food processing system, wherein the cold plasma is generated by a scalable cold plasma device capable of providing cold plasmas having dimensions from 25 cm through to at least 8 linear feet.

2. The method of claim 1, wherein the contacting the target substrate includes contacting a conveyer belt in the food processing system.

3. The method of claim 2, wherein the contacting the conveyer belt occurs when the conveyer belt is on its return path following conveyance of food.

4. The method of claim 1, wherein the contacting the target substrate includes using the multi-frequency harmonic-rich cold plasma produced by a dielectric barrier discharge (DBD) electrode device.

5. The method of claim 1, wherein the contacting the target substrate includes using the multi-frequency harmonic-rich cold plasma produced by an array of DBD electrode devices.

6. The method of claim 1, wherein the contacting the target substrate includes using the multi-frequency harmonic-rich cold plasma produced by an atmospheric pressure plasma jet device.

7. The method of claim 1, wherein the contacting the target substrate includes using the multi-frequency harmonic-rich cold plasma produced by an array of atmospheric pressure plasma jet devices.

8. The method of claim 1, wherein the contacting the target substrate with a multi-frequency harmonic-rich cold plasma includes using a DBD electrode device having an electrode length longer than 25 cm, or the effective area is in excess of 5 sq. cm.

9. The method of claim 1, further comprising:
    using a grounding assembly configured with the scalable cold plasma device to surround a food contact surface area.

10. The method of claim 1, further comprising:
    using a frame configured to support the scalable cold plasma device and to direct the cold plasma to food processing equipment.

11. The method of claim 1, further comprising:
    providing the scalable cold plasma device with an electrical voltage having two or more harmonic frequencies using a cold plasma power supply coupled to the scalable cold plasma device.

12. The method of claim 1, wherein the contacting the target substrate includes contacting food.

13. The method of claim 1, further comprising:
using a grounding assembly configured with the scalable cold plasma device to surround a food contact surface area, the grounding assembly having a shape associated with a particular application.

14. The method of claim 1, wherein the contacting the target substrate with the multi-frequency harmonic-rich cold plasma over the effective area for the effective amount of time includes using the effective amount of time sufficient to achieve sanitation at a conveyor belt speed in a food handling operation.

15. The method of claim 1, wherein the contacting the target substrate includes using the multi-frequency harmonic-rich cold plasma produced by a DBD electrode device, the DBD electrode device having an electrode of length at least 25 cm.

16. The method of claim 1, wherein the contacting the target substrate with the multi-frequency harmonic-rich cold plasma includes using a multi-frequency harmonic-rich cold plasma having a length of at least 8 linear feet generated from a single cold plasma power source.

17. The method of claim 1, further comprising:
using one or more grounding elements configured to tailor the multi-frequency harmonic-rich cold plasma to a predetermined shape, contour or region.

18. The method of claim 2, wherein the contacting the conveyer belt includes contacting a variable speed conveyer belt.

19. The method of claim 2, wherein the contacting the conveyer belt includes contacting a conveyer belt comprising a non-conductive surface.

20. The method of claim 4, wherein the DBD electrode device comprises a metallic tube shrouded in a dielectric coating.

21. The method of claim 20, wherein the dielectric coating comprises polytetrafluoroethylene (PTFE), delrin, polyethylene (PE), polypropylene (PP), quartz, or glass.

22. The method of claim 4, wherein the DBD electrode device includes an electrode having a cross-sectional shape that comprises a circular shape, polygonal shape or a planar shape.

23. The method of claim 1, further comprising:
contacting the target substrate with ultraviolet light from a fluorescent bulb.

24. The method of claim 1, wherein the multi-frequency harmonic-rich cold plasma results from a power supply that provides electrical energy across a multitude of frequencies to the scalable cold plasma device.

* * * * *

UNITED STATES PATENT AND TRADEMARK OFFICE
CERTIFICATE OF CORRECTION

PATENT NO.        : 9,295,280 B2
APPLICATION NO.   : 14/103540
DATED             : March 29, 2016
INVENTOR(S)       : Jacofsky et al.

It is certified that error appears in the above-identified patent and that said Letters Patent is hereby corrected as shown below:

Claims

Column 13, line 9, claim 14 replace "using the effective" with --using an effective--.

Column 14, line 15, claim 22 replace "polygonal shape" with --a polygonal shape--.

Signed and Sealed this
Fourteenth Day of June, 2016

Michelle K. Lee
*Director of the United States Patent and Trademark Office*